(12) United States Patent
Dove

(10) Patent No.: US 7,579,381 B2
(45) Date of Patent: Aug. 25, 2009

(54) TREATMENT OF BIOPROSTHETIC TISSUES TO MITIGATE POST IMPLANTATION CALCIFICATION

(75) Inventor: Jeffrey S. Dove, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 698 days.

(21) Appl. No.: 11/387,615

(22) Filed: Mar. 23, 2006

(65) Prior Publication Data

US 2006/0217805 A1 Sep. 28, 2006

Related U.S. Application Data

(60) Provisional application No. 60/665,618, filed on Mar. 25, 2005.

(51) Int. Cl.
- A61K 31/11 (2006.01)
- A61K 31/115 (2006.01)
- A61F 13/00 (2006.01)

(52) U.S. Cl. .................. 514/693; 514/694; 424/422
(58) Field of Classification Search .............. 514/693, 514/694; 424/422
See application file for complete search history.

(56) References Cited

U.S. PATENT DOCUMENTS

| | | | |
|---|---|---|---|
| 2,393,580 A | 1/1946 | Weiskopf |
| 3,002,895 A | 10/1961 | Freedman |
| 3,093,439 A | 6/1963 | Bothwell |
| 3,870,789 A | 3/1975 | Mikat |
| 3,927,422 A | 12/1975 | Sawyer |
| 3,961,097 A | 6/1976 | Gravlee, Jr. |
| 3,966,401 A | 6/1976 | Hancock et al. |
| 4,050,893 A | 9/1977 | Hancock et al. |
| 4,082,507 A | 4/1978 | Sawyer et al. |
| 4,120,649 A | 10/1978 | Schechter |
| 4,323,358 A | 4/1982 | Lentz et al. |
| 4,350,492 A | 9/1982 | Wright et al. |
| 4,372,743 A | 2/1983 | Lane |
| 4,402,697 A | 9/1983 | Pollock et al. |
| 4,405,327 A | 9/1983 | Pollock |
| 4,624,822 A | 11/1986 | Arru et al. |
| 4,648,881 A | 3/1987 | Carpentier et al. |
| 4,770,665 A | 9/1988 | Nashef |
| 4,786,287 A | 11/1988 | Nashef et al. |
| 4,800,603 A | 1/1989 | Jaffe |
| 4,885,005 A | 12/1989 | Nashef et al. |
| 4,911,713 A | 3/1990 | Sauvage et al. |
| 4,990,131 A | 2/1991 | Dardik et al. |
| 5,002,566 A | 3/1991 | Carpentier et al. |
| 5,068,086 A | 11/1991 | Sklenak et al. |
| 5,104,405 A | 4/1992 | Nimni |
| 5,116,564 A | 5/1992 | Jansen et al. |
| 5,131,908 A | 7/1992 | Dardik et al. |
| 5,275,954 A | 1/1994 | Wolfinbarger |
| 5,279,612 A | 1/1994 | Eberhardt |
| 5,447,536 A | 9/1995 | Girardot et al. |
| 5,595,571 A | 1/1997 | Jaffe et al. |
| 5,632,778 A | 5/1997 | Goldstein |
| 5,773,285 A | 6/1998 | Park |
| 5,792,603 A | 8/1998 | Dunkelman et al. |
| 5,882,918 A | 3/1999 | Goffe |
| 6,350,732 B1 | 2/2002 | Moore et al. |
| 2003/0125813 A1 | 7/2003 | Carpentier et al. |
| 2003/0226208 A1 | 12/2003 | Carpentier et al. |
| 2004/0030405 A1 | 2/2004 | Carpentier et al. |

FOREIGN PATENT DOCUMENTS

| | | |
|---|---|---|
| WO | WO 84/01894 | 5/1984 |
| WO | WO 95/11047 | 4/1995 |
| WO | WO 95/22361 | 8/1995 |
| WO | WO 95/34332 | 12/1995 |
| WO | WO 96/04028 | 2/1996 |
| WO | WO 96/13227 | 5/1996 |

OTHER PUBLICATIONS

European search letter for Application No. 06 739 363.7-1219: Mar. 2008.
International Search Report for Application No. PCT/US2006/010540 dated Jul. 5, 2007.
Allied Fischer Scientific Product Catologue, pp. 914, 1986.

*Primary Examiner*—Raymond J Henley, III
(74) *Attorney, Agent, or Firm*—Rajiv Yadav; Guy Cumberbatch

(57) ABSTRACT

The present invention provides methods for treating tissue to inhibit post-implant calcification of a biological tissue. In one method of this invention, a tissue is immersed in or otherwise contacted with a pretreated glutaraldehyde solution, i.e., a heat-treated or pH-adjusted glutaraldehyde solution. The tissue may be partially fixed with glutaraldehyde prior to, after, or concurrently with the step of contacting the tissue with the pretreated gluteraldehyde. Contact with the pretreated gluteraldehyde produces free amine groups on the tissue, which are subsequently blocked by contacting the crosslinked tissue with a blocking agent. In another embodiment, a tissue is contacted with either a non-pretreated glutaraldehyde or a pH-adjusted glutaraldehyde solution for a period of time sufficient to crosslink the tissue. The crosslinked tissue is then treated with a reducing agent that reduces aldehyde and carboxylic acid groups on the fixed tissue.

22 Claims, 2 Drawing Sheets

TREATMENT OF BIOPROSTHETIC TISSUES TO MITIGATE POST IMPLANTATION CALCIFICATION

CROSS REFERENCE TO A RELATED PATENT APPLICATION

Priority is herewith claimed under 35 U.S.C. §119(e) from co-pending Provisional Patent Application No. 60/665,618, filed Mar. 25, 2005, entitled "TREATMENT OF BIOPROSTHETIC TISSUES TO MITIGATE POST IMPLANTATION CALCIFICATION". The disclosure of this Provisional Patent Application is incorporated by reference herein in its entirety.

FIELD OF THE INVENTION

This invention pertains generally to medical methods/devices and more particularly to a method for fixing (e.g., tanning or crosslinking) and sterilizing biological tissue to decrease the fixed tissue's propensity for post-implantation calcification and decrease the thrombogenicity of the fixed tissue.

BACKGROUND OF THE INVENTION

Implantable biological tissues can be formed of human tissues preserved by freezing (i.e., cryopreserving) the so called homograft tissues, or of animal tissues preserved by chemically fixing (i.e., tanning) the so called bioprosthesis (Carpentier, Biological Tissues in Heart Valve Replacement, Butterworth (1972), Ionescu, Ed.). The type of biological tissues used as bioprostheses include cardiac valves, blood vessels, skin, dura mater, pericardium, small intestinal submucosa ("SIS tissue"), ligaments and tendons. These biological tissues typically contain connective tissue proteins (i.e., collagen and elastin) that act as the supportive framework of the tissue. The pliability or rigidity of each biological tissue is largely determined by the relative amounts of collagen and elastin present within the tissue and/or by the physical structure and configuration of its connective tissue framework. Collagen is the most abundant connective tissue protein present in most tissues. Each collagen molecule is made up of three (3) polypeptide chains intertwined in a coiled helical configuration.

The techniques used for chemical fixation of biological tissues typically involve the exposure of the biological tissue to one or more chemical fixatives (i.e., tanning agents) that form cross-linkages between the polypeptide chains within a given collagen molecule (i.e., intramolecular crosslinkages), or between adjacent collagen molecules (i.e., intermolecular crosslinkages).

Examples of chemical fixative agents that have been utilized to cross-link collagenous biological tissues include: formaldehyde, glutaraldehyde, dialdehyde starch, hexamethylene diisocyanate and certain polyepoxy compounds. Of the various chemical fixatives available, glutaraldehyde has been the most widely used since the discovery of its antiimmunological and antidegenerative effects by Dr. Carpentier in 1968. See Carpentier, A., *J. Thorac. Cardiovascular Surgery*, 58: 467-69 (1969). In addition, glutaraldehyde is one of the most efficient sterilization agents. Glutaraldehyde is used as the fixative and the sterilant for many commercially available bioprosthetic products, such as porcine bioprosthetic heart valves (e.g., the Carpentier-Edwards™ stented porcine Bioprosthesis), bovine pericardial heart valves (e.g., Carpentier-Edwards™ Pericardial Bioprosthesis) and stentless porcine aortic valves (e.g., Edwards PRIMA Plus™ Stentless Aortic Bioprosthesis), all manufactured and sold by Edwards Lifesciences LLC, Irvine, Calif.

Fixation provides mechanical stabilization, for example, by preventing enzymatic degradation of the tissue. Glutaraldehyde has been extensively employed as a cross-linking agent to react with amino acid residues of collagen, such as the $\epsilon$-amino groups of lysine and hydroxylysine or the carboxyl groups of aspartic acid and glutamic acid. The chemical nature of the glutaraldehyde-amine reaction is complex due to the reactivity of the glutaraldehyde molecule as well as the self-polymerization of dialdehydes. The most important component of the reaction products of an aldehyde and a primary amine involves the formation of a Schiff base wherein the nitrogen forms a double bond with the aldehyde carbon, replacing the double bond between the carbonyl carbon and the oxygen.

One problem associated with the implantation of many bioprosthetic materials is that the connective tissue proteins (i.e., collagen and elastin) within these materials can become calcified following implantation within the body. Such calcification can result in undesirable stiffening or degradation of the bioprosthesis. Two types of calcification—intrinsic and extrinsic—are known to occur in fixed collagenous bioprostheses. Intrinsic calcification follows the adsorption by the tissue of lipoproteins and calcium binding proteins. Extrinsic calcification follows the adhesion of cells (e.g., platelets) to the bioprosthesis and leads to the development of calcium phosphate-containing surface plaques on the bioprosthesis.

The factors that affect the rate at which fixed tissue bioprostheses undergo calcification have not been fully elucidated. However, factors thought to influence the rate of calcification include the patient's age, the existence of metabolic disorders (i.e., hypercalcemia, diabetes, etc.), dietary factors, the presence of infection, parenteral calcium administration, dehydration, in situ distortion of the bioprosthesis (e.g., mechanical stress), inadequate anticoagulation therapy during the initial period following surgical implantation and immunologic host-tissue responses.

In addition, glutaraldehyde fixation may have effect on tissue calcification. Further, in many cases, the fixed tissues are stored in media containing glutaraldehyde to maintain sterility. Unreacted glutaraldehyde or glutaraldehyde adsorbed during storage can leach out into the body post-implantation and cause side effects, as glutaraldehyde is suspected to be cytotoxic. In addition, unreacted aldehyde groups are typically present on the fixed tissue, which can become oxidized to carboxylic moieties. These moieties can attract calcium ions in vivo and contribute toward initiating calcification.

Efforts at retarding the calcification of bioprosthetic tissue have been numerous in recent years. The techniques resulting from these efforts may be broadly divided into two categories; those involving the pre- or post-treatment of glutaraldehyde-fixed tissue with one or more compounds that inhibit calcification (or modify the fixed tissue to be less prone to calcification) and those involving the fixation of the tissue with compounds other than glutaraldehyde, thereby reducing calcification.

The former category of techniques includes, but is not limited to, treatment with such compounds as: a) detergent or surfactant, after glutaraldehyde fixation; b) diphosphonates, covalently bound to the glutaraldehyde-fixed tissue or administered via injection to the recipient of the bioprosthesis or site-specifically delivered via an osmotic pump or controlled-release matrix; c) amino-substituted aliphatic functional acid, covalently bound after glutaraldehyde-fixation; d) sulfated polysaccharides, especially chondroitin sulfate, after glutaraldehyde fixation and preferably followed by treatment with other matrix-stabilizing materials; e) chitosan/heparin coupling after fixation; f) ferric or stannic salts, either before or after glutaraldehyde fixation; g) polymers, especially elastomeric polymers, incorporated into the glutaraldehyde-fixed tissue; or h) water-soluble solutions of a phosphate ester or a quaternary ammonium salt or a sulfated higher aliphatic alcohol, after glutaraldehyde-fixation.

The latter category of techniques for reducing the calcification of bioprosthetic tissue, i.e., techniques involving the fixation of the tissue with compounds other than glutaraldehyde, includes but is not limited to, the following: a) treatment by soaking the bioprosthetic tissue in an aqueous solution of high osmolality containing a photo-oxidative catalyst and then exposing said tissue to light thereby fixing the tissue via-photo-oxidization; and b) fixation via treatment with a polyepoxy compound, such as polyglycidyl ether (polyepoxy) compound.

Recently a new technique of calcium mitigation was described in U.S. Patent Publication No. 2003/0125813 A1, which is incorporated herein in its entirety. This method involves contacting fixed, unfixed or partially fixed tissue with a glutaraldehyde solution that has previously been heat-treated or pH adjusted prior to its contact with the tissue. Lee, et al. (*J. Biomed. Mater. Res.*, 58(1);27-35 (2001)) have disclosed a method of mitigating unreacted glutaraldehyde residues by blocking with amino compounds, e.g., $NH_2$—PEO—$SO_3$ or heparin containing amino groups.

Although some of these techniques have proven to be efficient in reducing calcification, there remains a need in the art for further improvements of the existing techniques or for the development of new calcification-mitigating techniques to lessen the propensity for post-implantation calcification of fixed bioprosthetic tissues.

SUMMARY OF THE INVENTION

The present invention provides methods for treating biological tissue to inhibit post-implant calcification of the tissue. According to one method of this invention, a tissue is immersed in or otherwise contacted with a pretreated glutaraldehyde solution. In a preferred embodiment of the present invention, the glutaraldehyde solution is pretreated by adjusting its pH to a pH within the range of about 5.0 to 7.0, and preferably to about 6.0. This pretreated glutaraldehyde solution is then used to treat the tissue, preferably at a temperature in the range of about 30 to 70° C., more preferably at a temperature between about 40 to 60° C., and most preferably, at a temperature of about 45 to 55° C. In a preferred embodiment, the tissue is treated for a period of time between about one hour to six months, and more preferably for about one day to two months. The tissue is at least partially fixed prior to, after, or concurrently with the step of contacting the tissue with the pretreated gluteraldehyde, wherein the tissue is fixed by immersing the tissue in a solution containing gluteraldehyde as a crosslinking agent. Contact with the pretreated gluteraldehyde produces free amine groups on the tissue, which are subsequently blocked by contacting the crosslinked tissue with a blocking agent.

In yet another embodiment of a method of the present invention, a tissue is contacted with either a glutaraldehyde solution or a pH-adjusted glutaraldehyde solution for a period of time sufficient to crosslink the tissue. The crosslinked tissue is first heated and then treated with a reducing agent that reduces aldehyde and carboxylic acid groups on the fixed tissue.

In each method of this invention, the pretreated glutaraldehyde solution may also be used as a terminal sterilization solution subsequent to the blocking step. In addition, the glutaraldehyde solution, whether pretreated or not, may also contain other chemicals to enhance its efficacy, such as surfactants (e.g., Tween 80), alcohol (e.g., ethanol) and/or aldehydes (e.g., formaldehyde).

Further in accordance with the invention, there are provided bioprosthetic devices or articles that are formed, wholly or partially, of tissue that has been treated in accordance with the various embodiments of the methods of the present invention. Examples of biological tissues of human or animal origin which may be used in bioprosthetic devices or articles of the present invention include, but are not limited to, heart valves, venous valves, blood vessels, ureter, tendon, dura mater, skin, pericardium, cartilage (e.g., meniscus), ligament, bone, intestine (e.g., intestinal wall), small intestinal submucosa ("SIS tissue"), and periostium.

Further in accordance with the present invention, there are provided methods for treating diseases and disorders of mammalian patients, by implanting bioprosthetic materials that have undergone the calcification mitigating treatment of the various embodiments of the method of the present invention. Such treatment methods include, but are not limited to, a) the surgical replacement of diseased heart valves with bioprosthetic heart valves that have been treated with glutaraldehyde in accordance with the present invention, b) the repair or bypassing of blood vessels by implanting biological vascular grafts that have been treated with glutaraldehyde in accordance with the present invention, c) the surgical replacement or repair of torn or deficient ligaments by implanting bioprosthetic ligaments that have been prepared in accordance with the present invention and, d) the repair, reconstruction, reformation, enhancement, bulking, ingrowth, reconstruction or regeneration of native tissues by implanting one or more biopolymeric or bioprosthetic tissue scaffolds that have been prepared in accordance with the present invention (e.g., tissue engineering with a natural tissue or biopolymeric scaffold).

The various embodiments of the method of mitigating post-implantation calcification of bioprosthetic tissues offer significant advantages over previous practices, as the desirable features of blocking the free amine groups or reducing aldehyde and acid functional groups lessens the potential for untoward or undesirable reactions between the fixed tissue and glutaraldehyde that is present in storage and/or sterilization solutions.

Also contemplated is the use of pH buffer formulations that contain antioxidants (e.g., ascorbic acid) that promote long-term, low acid stability for storage.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate preferred embodiments of the present invention and, together with the description, serve to explain the principles of the invention.

DETAILED DESCRIPTION OF THE INVENTION

Figure 1:
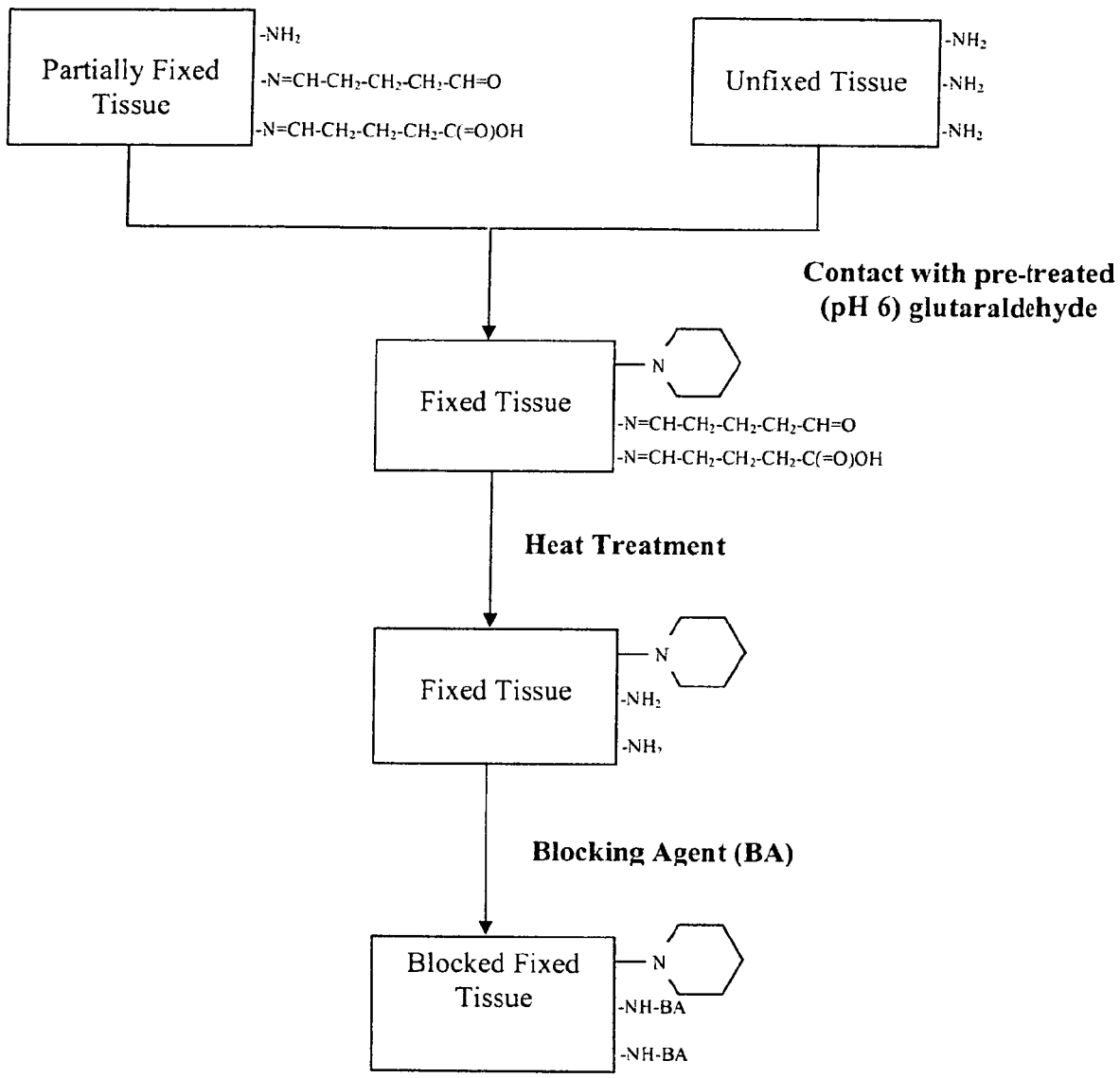
FIG. 1 is a flow diagram for mitigating calcification of a bioprosthetic tissue by blocking free amine groups on the tissue.

It has previously been reported that cross-linked bioprosthetic tissue post-treated in 0.625% glutaraldehyde phosphate solution for 2 months at 50° C., with fluid movement (e.g., shaking), exhibited less calcification in the rat subcutaneous and rabbit intramuscular implant models than control cross-linked bioprosthetic tissue fixed in 0.625% glutaraldehyde phosphate solution under typical conditions (i.e., room temperature for 1-14 days). See U.S. Pat. No. 5,931,969, which is specifically incorporated in its entirety herein by reference.

It has also been previously reported that it is advantageous to conduct the heating step on the glutaraldehyde solution prior to its contact with the tissue. See U.S. Publication Serial No. 2003/0125813, which is specifically incorporated in its entirety herein by reference. The heat-treated glutaraldehyde may then be cooled to a lower temperature and the tissue may then be added to the cooled glutaraldehyde solution under conditions of reduced severity, greater convenience, or both (e.g., shorter time, lower temperature, or both). By heat-treating the glutaraldehyde solution in the absence of the tissue, higher temperatures, concentrations or both can be used during the heat-treating process without risking or causing any adverse effect on the tissue.

It was also reported in U.S. Publication Serial No. 2003/0125813 that alternatively the glutaraldehyde solution can be buffered, rather than heat-treated, by adjusting the pH of the solution to within a range of about 5.0 to 7.0, preferably about 6.0. The buffered glutaraldehyde solution has a similar, although slightly less, advantageous effect as the heat-treated glutaraldehyde solution.

Since the above disclosures, Applicants have discovered that it is advantageous to remove carboxylic acid residues and aldehyde residues, which have the potential to be oxidized to carboxylic acids, from the fixed tissue, since it has been proposed that the carboxylic moiety attracts calcium ions and contributes towards initiating calcification of bioprosthetic tissue. Accordingly, in one method of this invention a tissue is immersed in or otherwise contacted with a glutaraldehyde solution (less than about 5% by weight). The tissue is at least partially fixed prior to, after, or concurrently with the step of contacting the tissue with the gluteraldehyde, wherein the tissue is fixed by immersing the tissue in a solution containing gluteraldehyde as a crosslinking agent. Contact with the solution in this manner hydrolyzes labile Schiff base bonds located at or near the surface of the collagen superhelix of the tissue, thus removing aldehyde and acid groups coupled to the tissue via the Schiff base bonds and producing free amine groups on the tissue. The Schiff base bonds deeper within the superhelix are sterically protected and therefore are not hydrolyzed. The free amine groups are then blocked in a subsequent step by contacting the crosslinked tissue with a blocking agent.

In an alternative embodiment of the present invention, the tissue is treated with a pretreated glutaraldehyde that is prepared by adjusting the pH of the glutaraldehyde solution to a pH within the range of about 5.0 to 7.0, and preferably to about 6.0. The tissue is at least partially fixed prior to, after, or concurrently with the step of contacting the tissue with the pH adjusted glutaraldehyde, wherein the tissue is fixed by immersing the tissue in a solution containing glutaraldehyde as a crosslinking agent. The pH-adjusted glutaraldehyde solution is then used to treat the tissue, preferably at a temperature in the range of about 30 to 70° C., more preferably at a temperature between about 40 to 60° C., and most preferably, at a temperature of about 45 to 55° C. In a preferred embodiment, the tissue is treated for a period of time between about one hour to six months, and more preferably for about one day to two months. Contact with the pH adjusted glutaraldehyde in this manner hydrolyzes labile Schiff base bonds located at or near the surface of the collagen superhelix, thus removing aldehyde and acid groups coupled to the tissue via the Schiff base bonds and producing free amine groups on the tissue. The free amine groups are then blocked in a subsequent step by contacting the crosslinked tissue with a blocking agent.

In yet another embodiment of a method of the present invention, the tissue is contacted with an untreated or pH adjusted glutaraldehyde solution without heating for a period of time sufficient to promote crosslinking. The crosslinked tissue is then treated with a reducing agent that reduces aldehyde and carboxylic acid groups coupled to the fixed tissue.

A. Method for Mitigating Calcification of Bioprosthetic Material Using Pretreated Glutaraldehyde FIG. 1 is a flow diagram that generally illustrates one embodiment of the method of the present invention. As shown in FIG. 1, the first step of the process is to prepare a pretreated glutaraldehyde solution, e.g., a heat-treated or pH adjusted glutaraldehyde, in the absence of tissue.

1. Preparation of Heat-treated Glutaraldehyde in Absence of Tissue

Briefly, a heat-treated glutaraldehyde solution is prepared in the absence of the tissue by heating the solution to a first temperature for a first period of time. The temperature of the glutaraldehyde solution is then adjusted to a second temperature (preferably lower than the first temperature) before contacting the tissue. However, this step may also be carried out with an aqueous solution or a solution of unheated glutaraldehyde.

It will be appreciated that the concentration of glutaraldehyde in the starting solution may be varied. Thereafter, the solution concentration may be adjusted, if desired, prior to addition of the tissue. It is believed that glutaraldehyde concentrations of as little as 0.1% and as much as 25% or more may be used during the heat-treating step. Reduced glutaraldehyde concentrations of 0.6% to 2.5% have, to date, been successfully obtained and used by Applicant, and those skilled in the art will recognize that higher or lower concentrations of glutaraldehyde may indeed prove to be advantageous during the heat-treating step of the process. The preferred concentration for use during the heat-treating step (FIG. 1) is 1.0-2.0%. This heat-treatment of the glutaraldehyde may be accomplished by heating of the solution until the free aldehyde content of the solution has fallen about 25% or more and remains stable at that level (e.g., a solution of 1.8% falls to about 0.6% or less). Initially, the solution containing glutaraldehyde may be buffered to a pH of 7.4 with a phosphate buffer, a non-phosphate buffer such as a HEPES buffer, or other suitable buffered solutions, and, in such cases, heating of the solution to cause the free aldehyde content to fall will also cause the pH of the solution to fall.

In one embodiment, an aqueous solution of 1.8% by weight glutaraldehyde is prepared in a clean, inert vessel (e.g., a vessel made of stainless steel, plastic or borosilicate glass) and such solution is then buffered to the pH of approximately 7.4 by adding phosphate buffered saline solution.

The first temperature to which the glutaraldehyde is heated is sufficiently high, and is maintained for sufficiently long, to cause the free aldehyde content and pH of the glutaraldehyde solution to fall by a predetermined amount. Preferably, the prior heat-treating of the glutaraldehyde solution causes the free aldehyde concentration of the solution to decrease by about 25%, more preferably by about 50%. The glutaraldehyde solution may be buffered so that the pH is initially in the range of about 7.2 to 7.8, preferably about 7.4. After the heating has been carried out, the pH of the solution will typically have fallen to approximately 5.0 to 7.0, preferably 6.0. Due to the preheating of the glutaraldehyde solution, the solution does not significantly change its chemical characteristics when used to treat the tissue later in the procedure.

The heat-treatment of the glutaraldehyde may be accomplished by any suitable means. For example, the glutaraldehyde can be pre-heated to and maintained at a temperature between about 20 to 90° C., preferably between about 60 to 80° C., and most preferably 65 to 75° C. for a period of time sufficient to cause the free aldehyde concentration to decrease by at least 25% and until the pH of the solution falls to approximately 6.0 (i.e., the pH of 6.0 corresponds to a free aldehyde concentration of about 0.3-0.7%). At this point, the color of the solution can be colorless to golden or brown. The fall of the solution pH to 6.0 and the accompanying change in color to golden or brown indicates that the preheating treatment has been completed. Depending on the temperature used, the step of heat treating the glutaraldehyde may take anywhere from one hour to six months or more depending on the temperature used, and typically between 1-14 days. The preferred method is to heat the glutaraldehyde solution to approximately 65 to 75° C., for approximately 1 day to 2 months or until the desired fall of at least 25% or more in free aldehyde concentration and a pH of approximately 6.0, are observed. Higher temperatures ranging up to approximately 90° C. may be used, and the use of such higher temperatures will typically speed the desired fall in free aldehyde concentration and accompanying change in pH (e.g., a solution having a starting pH adjusted to 7.4 will fall to a pH of about 6.0 after approximately 1-3 days at 90° C.). Lower temperatures, ranging downward to approximately 20° C., may also be used, and the use of such lower temperatures will typically cause the desired free aldehyde content and pH changes to take longer.

After the heat-treatment of the glutaraldehyde has been completed the solution is filtered and cooled to a second temperature that does not cause damage to the tissue (e.g., about 30 to 70° C., preferably about 40 to 60° C., or most preferably at about 50° C.).

Optionally, after the glutaraldehyde has been heat-treated, the solution is allowed to cool to about 50° C. and its pH is adjusted to approximately 7.4 by adding phosphate buffered saline or some other suitable buffer.

2. Preparation of pH Adjusted Glutaraldehyde

In another embodiment of this invention, the glutaraldehyde solution is not pre-heated, but rather the pH of the glutaraldehyde solution is adjusted to a pH within the range of about 5.0 to 7.0, and preferably to about 6.0.

3. Harvesting and Preparation of Tissue

The desired biological tissue is harvested from a human cadaver or animal donor, and prepared for subsequent fixation and treatment. The tissue is typically harvested by surgical cutting or removal from its host animal. Thereafter, it is typically trimmed or cut to size and washed with sterile water, basic salt solution, saline or other suitable washing solution.

In one embodiment, the tissue may be heat treated in a surfactant solution (e.g., Tween 80 with or without ethanol and/or formaldehyde) or in a physiologic solution (e.g. saline or a balanced salt solution) prior to fixation at a temperature between about 37° C. and 60° C., preferably about 45° C., for about one hour to six months, preferably about one to 15 days, and then heat treated in a heat treated glutaraldehyde solution as described above.

In one embodiment, the tissue is treated with a surfactant prior to fixation to remove lipids, fatty acids, cholesterol, etc. to ensure that the tissue will be fixed throughout rather than merely on the surface. However, care must be taken not to overdo the cleaning action and thereby damage the base tissue by using too strong a solution. Thus, it is preferred to use the surfactant in the form of an aqueous solution containing 0.5 to 6% by weight of surfactant. A suitable treatment time is from two to six hours, preferably about three hours (See U.S. Pat. No. 4,553,974, which is incorporated in its entirety herein by reference). The surfactant may be an anionic surfactant, a non-ionic surfactant, an amphoteric surfactant or a mixture thereof. Examples of suitable anionic surfactants are sodium dodecyl sulfate, sodium dodecyl sulfoacetate and sodium salt of alkaryl polyether sulfonate. Examples of suitable non-ionic surfactants are octylphenoxy polyethoxy ethanol (Triton X-100), polyoxyethylene (20) sorbitan monooleate (Tween 80), polyoxyethylene (20) sorbitan monostearate (Tween 60). Examples of suitable amphoteric surfactants are sulfobetaines commonly known as Zwittergents.

Alternatively, lipids are removed by immersing the tissue in a high osmolality aqueous solution, such as a solution of a salt and a sugar, wherein the salt is capable of penetrating the sample and the sugar functions to maintain the high osmolality of the solution as described in U.S. Pat. No. 6,350,732, which is incorporated in its entirety herein by reference. Examples of suitable salts include, but are not limited to, sodium chloride and potassium chloride, and examples of suitable sugars include, but are not limited to, sucrose and fructose.

4. Fixation of Biological Tissue

The biological tissue may be fixed prior to, during, or after its treatment with the pretreated glutaraldehyde. In the example illustrated in FIG. 1, the tissue is fixed prior to undergoing the treatment with pretreated glutaraldehyde. In this example the fixation is carried out by immersing the tissue in a solution of 0.625% by weight glutaraldehyde buffered to a pH of approximately 7.4 by a suitable buffer such as a phosphate buffer, for 1-14 days at ambient temperature.

Preferably, tissue fixation is carried out by immersing the tissue in a solution comprising a glutaraldehyde solution that has a low acid-forming potential, such as high purity glutaraldehyde monomer (molecular weight (MW) 100), high purity glutaraldehyde dimer (MW 182), a mixture of the two, low acid dialyzed or commercial gluteraldehyde.

In order to enhance fixation or sterilization, other chemical compounds such as surfactants (e.g. Tween 80) and/or ethanol and/or formaldehyde can be added to the glutaraldehyde.

After the tissue is removed from the fixative solution, it is thoroughly rinsed with saline solution, basic salt solution, free glutaraldehyde solution, or some other suitable washing solution.

5. Heat Treatment of Unfixed, Partially-fixed, or Fixed Tissue

The unfixed, partially fixed, or fixed tissue is then contacted with a pretreated glutaraldehyde solution (either heat-treated or pH adjusted) prepared as described above. Tissue that has been "fully fixed" in this regard means that the tissue has been fixed to an extent suitable for use as an implant, while "partially fixed" means that the tissue has been fixed to some extent short of being fully fixed.

The tissue treatment step according to the example in FIG. 1 is preferably accomplished by immersing fixed, partially fixed or unfixed tissue in the pretreated glutaraldehyde solution while maintaining the solution at about 30 to 70° C., preferably about 40 to 60° C., or most preferably at about 50° C., with or without fluid movement. It is preferable that the pH of the solution be left at about 6.0 prior to placement of the tissue within the solution. Thereafter, the temperature of the solution is maintained at approximately 50° C. with the tissue immersed in the solution to allow the pretreated glutaraldehyde solution to interact with or modify the tissue. The tissue's susceptibility to post-implant calcification will be significantly reduced after immersion in the pretreated glutaraldehyde for as little as one hour to as much as six months or more (depending primarily on the temperature used), but typically occurs within 1 to 15 days at 50° C. Thereafter, the tissue is removed from the solution. The tissue is typically brown in color at this time. After it has been removed from the pretreated glutaraldehyde solution, the tissue is thoroughly rinsed with saline solution, basic salt solution, or some other suitable washing solution.

6. Blocking Free Amine Groups

One end result of treating the tissue with glutaraldehyde is the hydrolysis of the carbon-nitrogen double bonds of the less stable Schiff base bonds on and/or near the surface of the tissue, thereby simultaneously removing aldehyde and acid groups that were coupled to the tissue via the Schiff base bonds. This is desirable, since the unreacted aldehyde groups can become oxidized to carboxylic moieties, which then attract calcium ions in vivo and contribute toward initiating calcification. However, the treatment with glutaraldehyde results in a cross-linked tissue with free amine residues at and/or near the surface of the tissue.

Because since hydrolysis of the Schiff base bonds also results in the presence of primary amine residues on the tissue that could react with glutaraldehyde present in the post-sterilization and storage solutions (FIG. 1), the present inventors discovered that it is advantageous to contact the primary amines with a solution comprising a blocking reagent that will react with and block the primary amine, thus avoiding reactions between free amines and glutaraldehyde that is present in solutions used in subsequent steps according to this invention. This in turn reduces the amount of free aldehyde groups coupled to the tissue that could potentially get oxidized to acids. Therefore, after treatment with the pretreated glutaraldehyde, the tissue is rinsed and then contacted with a blocking agent (FIG. 1). As used herein, a "blocking agent" is any compound having a functional group or chemical moiety that is sufficiently reactive with an amine group. Blocking agents reactive with an amine group and suitable for use in this invention include, but are not limited to, monoaldehydes (i.e., a molecule containing a single aldehyde functionality, such as formaldehyde), sugars, water-soluble polyepoxys such as ethylene glycol diglycidyl ether (also know as Denacol), collagen, and any other agents known in the art that contain amine reactive functionalities, provided the product of the reaction between the amine group and the blocking agent does not contain a free aldehyde or carboxylic acid group.

For example formaldehyde, which has a single aldehyde functional group, can react with a primary amine on the tissue to form a Schiff base bond wherein the nitrogen of the primary amine forms a double bond with the formaldehyde carbonyl carbon. In contrast to the reaction between a primary amine and glutaraldehyde, a Schiff base bond formed from a reaction between a primary amine and formaldehyde does not have a free aldehyde moiety that can become oxidized to a carboxylic acid, and therefore blocking the amine with formaldehyde will not increase the propensity of the tissue towards calcification post-implantation. A further advantage of utilizing formaldehyde as the blocking reagent is that the Schiff base bond will slowly hydrolyze post-implantation, thereby releasing formaldehyde into the region surrounding the implanted tissue. The slow-released formaldehyde will depress hyperplasia on the tissue implant (i.e., an abnormal increase in the number of tissue cells) and therefore will reduce or prevent an overgrowth of tissue on the implanted bioprosthetic tissue.

Another example of a suitable blocking agent is a polyglycidyl ether, which readily reacts with amines. Examples of polyglycidyl ether blocking agents include, but are not limited to, any of the various Denacols and their individual reactive species, including mono, di, tri, and multi-functional epoxides.

Sugars also react with amines and therefore are also suitable as blocking agents according to this invention. Suitable sugars include reducing sugars, which can form Schiff base bonds with the free amine groups on the tissue. Examples of reducing sugars include, but are not limited to, glycerose, threose, erythrose, lyxose, xylose, arabinose, ribose, allose, altrose, glucose, mannose, gulose, idose, galactose, talose, or any other diose, triose, tetrose, pentose, hexose, septose, octose, nanose or decose.

Figure 2:
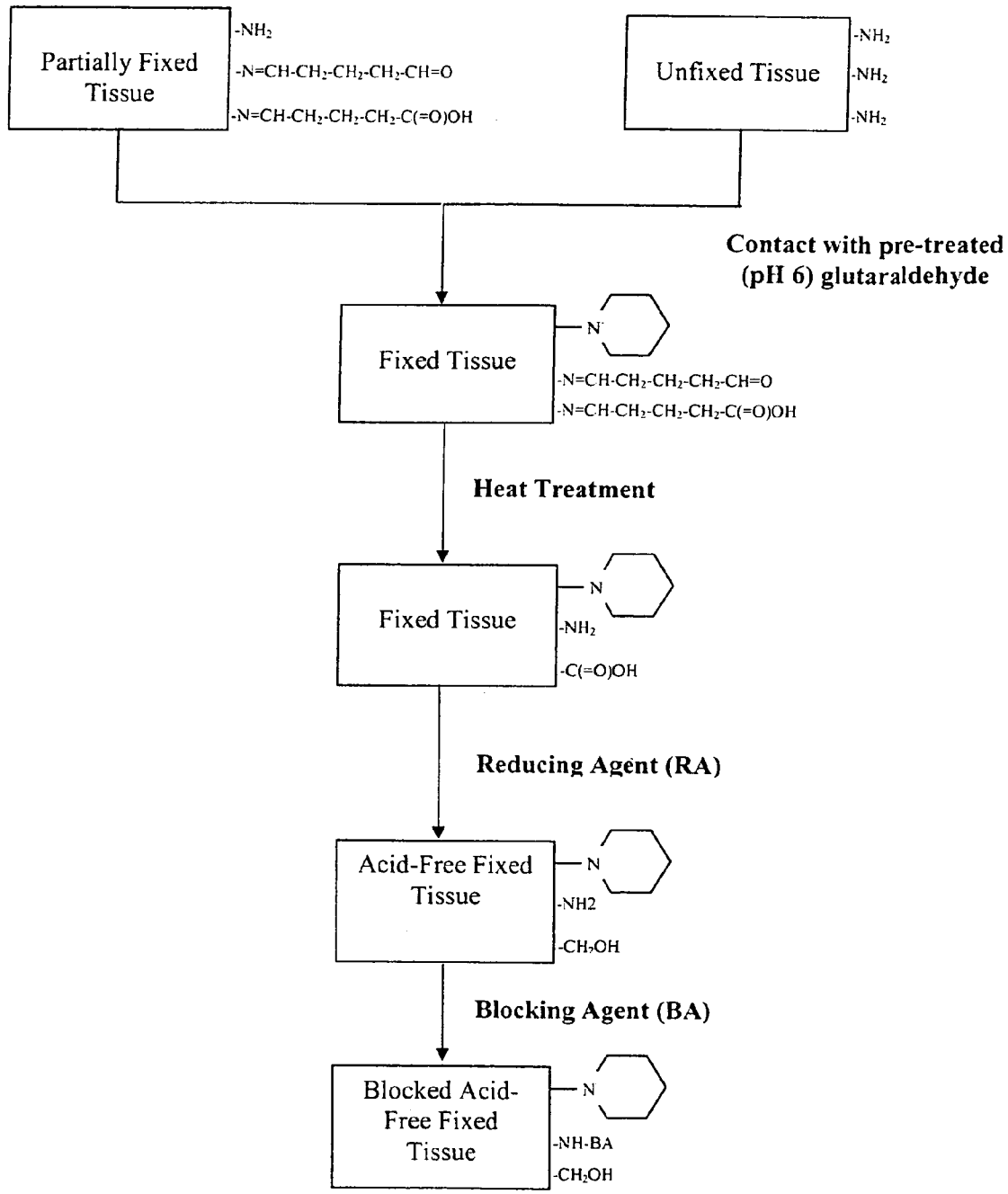
FIG. 2 is a flow diagram for mitigating calcification of a bioprosthetic tissue by reducing aldehyde and acid groups coupled to the tissue.

B. Method for Mitigating Calcification of Bioprosthetic Material Using Untreated or pH-adjusted Glutaraldehyde and Subsequent Reduction An alternative method of the present invention is illustrated in FIG. 2.

A biological tissue is harvested from a human cadaver or animal donor, and prepared for subsequent fixation and treatment as described herein. The tissue is optionally treated with a surfactant or a high osmolality aqueous solution prior to fixation to remove lipids, fatty acids, cholesterol, etc. to ensure that the tissue will be fixed throughout rather than merely on the surface as described herein.

The tissue is then contacted with either a non-pretreated glutaraldehyde or a pH-adjusted glutaraldehyde solution wherein the pH is within the range of about 5.0 to 7.0, and preferably to about 6.0 for a period of time sufficient to crosslink the tissue. The crosslinked tissue is then treated with a reducing agent that reduces aldehyde and carboxylic acid groups coupled to the fixed tissue. In this the crosslinked tissue is treated with a reducing agent that will reduce carboxylic acid or potential acid-forming functional groups such as aldehydes. Removing all or substantially all of the carboxylic acid and/or potential acid forming functional groups on the crosslinked tissue thus removes potential nucleation sites for calcification to occur.

Although in theory any reducing agent that will effectively reduce carboxylic acid and aldehyde functional groups may be used for this step, for example, hydrides, thiols, formic acid, etc., preferably the reducing agent is a borohydride, and more preferably sodium borohydride. Other reducing agents include hydrogen, i.e., as used in standard reduction methods that utilize hydrogen, typically under pressure and 1-ethyl-3-(3-dimethylaminopropyl)carbodiimide (EDAC). It is known to those skilled in the art to use EDAC with N-Hydroxysuccinimide (or alternatively, N-Hydroxysulfosuccinimide) (NHSS) to improve yields. EDAC will "reduce" (couple) any free carbonyl group by coupling to any available amine and, therefore, it can also be used as a blocking agent for amines.

C. Additional Calcification Mitigation Procedures

It is known that the presence of ions such as phosphate ions tends to increase the occurrence of calcification. Therefore, the buffers or solutions used in any or all of the process steps of a method of this invention preferably include a buffer or antimineralization solution having a level of phosphates, sulfates, carbonates, calcium, and/or magnesium decreased to an amount effective in reducing calcification of the tissue after implantation. In one embodiment, the buffer is a phosphate-deficient solution. The phosphate-deficient solution has a level of phosphate decreased to an amount effective in reducing calcification of said tissue after implantation, said solution further being non-destructive or non-destabilizing to the tissue. Substantially phosphate-free solutions are those containing only trace amounts of phosphates, as in contaminating amounts found in most chemicals used in the preparation of conventional tissue-treating solutions. Examples of phosphate-deficient solutions include, but are not limited to, borate, bicarbonate, cacodylate, HEPES, MPRS, and PIPES. Other examples of antimineralization solutions or buffers include, but are not limited to, sodium chloride, ascorbic acid, and glutaric acid solutions.

In another embodiment, the buffer solutions utilized in any or all of the process steps of the methods of this invention include a non-isotonic buffer, that is, either hypertonic or hypotonic buffer, wherein the osmolality of the buffer has been adjusted to induce the desired tissue properties (e.g., density, modulus, tensile strength, elongation, etc.). For example, a hypertonic buffer (i.e., a buffer with a higher salt concentration than in normal cells) will pull water out of the tissue. As a result, the tissue components are pulled closer together, which allows them to cross-link easier and thus increases the density. Alternatively, a hypotonic buffer (i.e., a buffer with a lower salt concentration than in normal cells) will swell the tissue and allow deeper penetration of the cross-linking agent.

In another embodiment, one or more of the steps of the methods of this invention is performed under non-oxidizing conditions, including, but not limited to, performing the steps under a nitrogen blanket, low actinic safety lights, and/or mechanical covers.

D. Post-sterilization, Assembly/Fabrication and Storage of Bioprosthesis

1. First Bioburden Reduction (BREP I)

After the tissue has been fixed, treated to mitigate post-implant calcification according to a method of this invention, and rinsed, it is subjected to a first bioburden reduction treatment. For Example, the tissue is immersed in or otherwise contacted with a mixture containing i) a crosslinking agent, ii) a denaturing agent and iii) a surfactant (i.e., a CDS solution). One preferred CDS solution (described in U.S. Pat. No. 4,885,005 and U.S. Pat. No. 4,648,881, each of which is incorporated herein by reference) is a mixture of i) formaldehyde, ii) ethanol and iii) surfactant (e.g., Tween 80™ surfactant, available from ICI Americas, Brantford, Ontario). Such preferred CDS solution may also be referred to by the acronym "FETS" and has a preferred formulation as follows: Formaldehyde (4.0±0.4% by weight), Ethanol (22.0±2.2% by weight) and Tween (80 1.2±0.2% by weight). The tissue is preferably immersed in the CDS solution for 2 hours to 7 days and typically about 2 hours. During this immersion period, the CDS solution is maintained at a temperature of 4-50° C., and preferably at about 20-37° C.

Those skilled in the art will appreciate that various alternative chemical compounds or solutions may be substituted for each component of the CDS solution, as described below.

Potential alternative denaturing agents include, but are not limited to: alcohols/solvents: (e.g., ethanol, or isopropyl alcohol); acidified ethers (e.g., sulfuric acid/ether mixture, acetone, ethers of small alkyl size such as methyl, ethyl, etc.); ketones (e.g., methyl ethyl ketone): commercial solvent systems (e.g., Genesolve™ (Allied Signal, Inc., Morristown, N.J.)); glycols (e.g., glycerol ethylene glycol, polyethylene glycol, low molecular weight carbowax; and high concentration salt solutions (e.g., magnesium chloride, and sodium chloride).

Potential alternative surfactants include, but are not limited to:

a) anionic surfactants: e.g., esters of lauric acid, including but not limited to sodium laurel sulfate (also called sodium dodecyl sulfate); and alkyl sulfonic acid salts (e.g., 1-decanesulfonic acid sodium salt).

b) non-ionic compounds: e.g., compounds based on the polyoxyethylene ether structures, including Triton X-100, 114, 405, N-101 (available commercially from Sigma Chemical, St. Louis, Mo.) and related structures; Pluronic and Tetronic surfactants (available commercially from BASF Chemicals, Mount Olive, N.J.).

c) alkylated phenoxypolyethoxy alcohols: e.g., NP40, Nonidet P40, Igepal, CA630, hydrolyzed/functionalized animal and plant compounds including Tween 80, Tween 20, octyl-derivatives, octyl β-glucoside, octyl b-thioglucopyranoside, deoxycholate and derivatives thereof, zwitterionic compounds, 3-([cholamidopropyl]-dimethyl amino)-1-propanesulfonate (CHAPS), 3-([cholamidopropyl]-dimethyl amino)-2-hydroxy-1-propanesulfonate (CHAPSO) (available from Pierce Biotec Company, Rockford, Ill.).

The above surfactant compounds can be used individually or in mixtures such as deoxycholate/Triton or commercially available mixtures such as Micro-80/90.

2. Fabrication/Assembly

After the first bioburden reduction has been completed, the tissue may again be rinsed with a suitable rinsing solution such as isotonic saline or 0.625% glutaraldehyde and transported into a clean room or aseptic environment. Thereafter, the tissue may be further trimmed or shaped (if necessary) and attached to or assembled with any non-biological components (e.g., stents, frames, suture rings, conduits, segments of polyester mesh to prevent suture tear-through, etc.) to form the desired bioprosthetic device. Examples of bioprosthetic devices that are assembled of both biological tissue and non-biological components include stented porcine bioprosthetic heart valves (e.g., the Carpentier-Edwards™ Bioprosthesis), and bovine pericardial heart valves (e.g., Carpentier-Edwards™ Pericardial Bioprosthesis), stentless porcine aortic valves that incorporate fabric reinforcements (e.g., Edwards PRIMA PLUS™ Stentless Aortic Bioprosthesis), and conduit valves for bio-mechanical ventricular assist devices (e.g., the Novacor N-100PC model), all available from Edwards Lifesciences LLC, Irvine, Calif.

3. Second Bioburden Reduction (BREP II)

After the bioprosthesis has been fabricated and assembled it is subjected to a second bioburden reduction that is essentially a repeat of the first bioburden reduction described above, however, in this second bioburden reduction step, the solution is preferably maintained at about 37° C. for approximately 2 hours to 10 days, preferably about 9 hours.

4. Terminal Sterilization and Storage

After completion of the second bioburden reduction, the tissue (or bioprosthesis) is rinsed with a suitable rinsing solution (such as isotonic saline or 0.625% glutaraldehyde solution) and then placed in a terminal solution for storage and sterilization. A preferred terminal sterilization solution is a glutaraldehyde solution having a concentration of about 0.2 to 1.0% by weight glutaraldehyde, and most preferably about 0.625% by weight glutaraldehyde. This solution has a strong sterilizing effect that can be enhanced by a terminal heating of the solution.

In one embodiment of the terminal sterilization step, the tissue (or bioprosthesis) is immersed in or contacted with the terminal sterilization solution and heated for a period of time sufficient to ensure sterility of the bioprosthesis until the time of implantation. The period of heating varies depending upon the temperature utilized, i.e., the lower the temperature the longer the period of time. For example, from 1 or 2 hours to 1 month for temperatures between about 50° C. and 20° C., respectively. Preferably, the period of time is 1 to 6 days at 37° C. or 6 hours to 2 days at 50° C., however one of skill in the art will recognize that these temperature or time values can be modified within the scope of the invention.

In order to avoid additional transfer and manipulation, the terminal sterilization is preferably carried out in the sealed storage container or package in which the bioprosthesis will be shipped and stored until the time of implantation. The tissue (or bioprosthesis) is aseptically deposited in the storage container that has been pre-filled with the 0.625% glutaraldehyde aqueous solution buffered to a pH of 7.4 with sodium hydroxide, such that the tissue (or bioprosthesis) is fully immersed in the buffered glutaraldehyde solution. Thereafter, the container is sealed and placed at room temperature for at least 7 days, or in an oven at 37° C. for 24 hours, or at 50° C. for 6 hours to enhance the sterilization power of glutaraldehyde. Thereafter, the container is cooled to room temperature and shipped to the hospital or other location(s) where it is stored until the time of use of the bioprosthesis.

In another embodiment, the tissue is sterilized by an in-container terminal sterilization process comprising the steps of: providing a container which contains a quantity of a terminal sterilant solution comprising 0.2-1.0% by weight glutaraldehyde buffered to a pH of approximately 7.4; immersing the tissue in the terminal sterilant solution within said container; sealing the container; heating the container, the terminal sterilant solution and bioprosthesis contained therein to a temperature of about 37-50° C. for a period of about six hours to six days; cooling the container, the terminal sterilant solution and the bioprosthesis contained therein to room temperature; and allowing the container to remain sealed until it is desired to implant the bioprosthesis in a mammalian patient.

In another embodiment, the terminal sterilization is carried out before placing the tissue or bioprosthesis in the storage container.

In some cases, glutaraldehyde that has been heat-treated in accordance with this invention may be used as the terminal solution and, in such cases, it may be possible to shorten or completely eliminate the previous step of immersing the tissue in previously heat-treated glutaraldehyde, opting instead to accomplish some or all of the treatment of the tissue according to the methods of this invention until the last step of storage, i.e., concurrently with the terminal sterilization step.

In a preferred embodiment, the tissue with which the present method is practiced includes substantially any mammalian tissue that is useful in preparing a prosthetic device having a biological component thereto. For example, in one embodiment, the tissue is derived from an organ. In another embodiment, the tissue is selected from nerve tissue, glandular tissue (e.g., lymphatic tissue), respiratory tissue, digestive tissue, urinary tract tissue, sensory tissue (e.g., cornea, lens, etc.), and reproductive tissue. In a related embodiment where the biological material is a biological fluid, however, addition of liquid is not likely to be necessary, unless to dilute the ionic strength of the biological fluid to permit miscibility of the extraction solvent.

In presently a preferred embodiment, the tissue is selected from muscle tissue, adipose tissue, epithelial tissue and endothelial tissue. In particularly preferred embodiments, the tissue is selected from myocardial tissue and vascular tissue.

In a related embodiment, the tissue is selected from the group including, without limitation, heart valve, venous valve, blood vessel, ureter, tendon, dura mater, skin, pericardium, intestine (e.g., intestinal wall), or periostium. In a particularly preferred embodiment, the tissue is derived from bone, cartilage (e.g. meniscus), tendon, ligament, or any other connective tissue.

As the source of the material used for this purpose may vary with regard to both tissue type, the source may also vary with regard to species type (autologous, homologous or heterologous tissue). The artisan will appreciate that the methods of the present invention may be used with bioprosthetic devices that include one or more types of tissues or materials.

In a preferred embodiment where the biological material is a solid tissue or product, it may first be suspended in an aqueous solution so that it will be suitable for the extraction process. For example, brain tissue may be suspended in sucrose solution (e.g., 0.32 M sucrose) at 10% weight to volume. Other hypotonic or isotonic solutions include 5% dextrose, phosphate buffered saline, tri-buffered saline, HEPES-buffered saline, or any of the foregoing buffers. The biological material in the aqueous solution can also be homogenized, ground, or otherwise disrupted to maximize contact between the treatment agents and the biological material.

In a particularly preferred embodiment, the biological material will form part or all of a bioprosthetic tissue that is designed and intended for implantation into a graft recipient.

In yet another preferred embodiment, the structural integrity of the tissue is maintained. Structural integrity can be defined as the ability of tissue to perform it's necessary biological function. The artisan will appreciate that the degree of structural integrity required for the tissue to perform it's necessary function may vary among different types of tissues. Further, particular applications for which the tissue is used may require different levels of structural integrity.

The foregoing description is provided for the purpose of describing and illustrating a few exemplary embodiments of the invention only. One skilled in the art will recognize that other embodiments of the invention are possible, but are not described in detail here. Thus, these examples are not intended to limit the scope of the invention in any way. Unless defined otherwise, all technical and scientific terms used herein have the same meaning as commonly understood by one of ordinary skill in the art to which this invention belongs. Although the preferred methods and materials are now described any methods and materials similar or equivalent to those described herein can be used in the practice or testing of the present invention. The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

EXAMPLES

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A method for mitigating post-implantation calcification of a bioprosthetic material, said method comprising
   (a) adjusting the pH of a glutaraldehyde solution to a pH in the range of about 5.0 to 7.0;
   (b) contacting a quantity of biological tissue that contains connective tissue protein with the glutaraldehyde solution;
   (c) heating the glutaraldehyde solution and the tissue to a temperature in the range of about 30 to 70° C. for a period of time, thereby producing free amine groups on the tissue, wherein the tissue is
      (i) at least partially fixed prior to the performance of Step (c),
      (ii) fixed after the performance of Step (c), or
      (iii) fixed concurrently with the performance of Step (c), and wherein said tissue is fixed by immersing the tissue in a crosslinking solution comprising gluteraldehyde as a crosslinking agent; and
   (d) contacting the fixed tissue with a solution containing a blocking reagent that blocks the free amine groups.

2. The method of claim 1, wherein the pH is adjusted to about 6.0.

3. The method of claim 1, wherein the temperature is in the range of about 40 to 60° C.

4. The method of claim 1, wherein the period of time is between about one hour and six months.

5. The method of claim 1, wherein said blocking agent has a functional group that is reactive with the free amine groups.

6. The method of claim 1, wherein said blocking agent is a monofunctional aldehyde, a polyepoxy, a sugar, or collagen.

7. The method of claim 6, wherein said monofunctional aldehyde is formaldehyde.

8. The method of claim 6, wherein said polyepoxy is ethylene glycol diglycidyl ether.

9. The method of claim 1, wherein said glutaraldehyde has a low acid content.

10. The method of claim 1, wherein said crosslinking solution includes a non-isotonic buffer.

11. The method of claim 10, wherein said non-isotonic buffer is a hypotonic buffer.

12. The method of claim 1, further comprising contacting the tissue with a surfactant or a high osmolality aqueous solution of a salt and a sugar prior to Step (a).

13. The method of claim 1, further comprising subjecting the tissue to a bioburden reduction.

14. The method of claim 13, wherein the bioburden reduction process comprises contacting the tissue with a bioburden reduction solution containing a surfactant, and aldehyde and an alcohol.

15. The method of claim 1, further comprising sterilizing the bioprosthesis.

16. The method of claim 15, wherein the sterilization comprises contacting the bioprosthesis with a terminal sterilization solution and heating said terminal sterilization solution to a temperature between about 20 to 50° C. for a period of time sufficient to ensure the sterility of the bioprosthesis until the time of implantation.

17. The method of claim 16, wherein said terminal sterilization solution comprises an aqueous solution of 0.2-1.0% by weight glutaraldehyde buffered to a pH of approximately 7.4.

18. The method of claim 16, wherein the terminal sterilization solution comprises osmotically balanced salt solution in combination with at least one chemical sterilant.

19. The method of claim 1, further comprising storing the bioprosthetic in a storage solution comprising gluteraldehyde and an antioxidant.

20. The method of claim 19, wherein said antioxidant is ascorbic acid.

21. The method of claim 1, wherein one or more of said steps is performed under non-oxidizing conditions.

22. The method of claim 21, wherein said non-oxidizing conditions are selected from the group consisting of;
   a nitrogen blanket;
   low actinic safety lights; and
   mechanical covers.

* * * * *